United States Patent
Wunderink et al.

(10) Patent No.: US 6,294,339 B1
(45) Date of Patent: Sep. 25, 2001

(54) METHOD OF DIAGNOSING AND TREATING INCREASED RISK OF DEATH FROM COMMUNITY-ACQUIRED PNEUMONIA ASSOCIATED WITH THE A ALLELE OF THE TNFα-238 POLYMORPHISM

(76) Inventors: Richard Glenn Wunderink, 8363 Barncliff Cove, Germantown, TN (US) 38139; Grant William Waterer, 3/13 Hayes Ave., Yokine 6060 (AU)

(*) Notice: Subject to any disclaimer, the term of this patent is extended or adjusted under 35 U.S.C. 154(b) by 0 days.

(21) Appl. No.: 09/745,005

(22) Filed: Dec. 21, 2000

Related U.S. Application Data
(60) Provisional application No. 60/238,976, filed on Oct. 10, 2000.

(51) Int. Cl.$^7$ .................................................. C12Q 1/68
(52) U.S. Cl. ..................... 435/6; 435/4; 435/5; 435/6; 435/91.1; 435/91.2; 435/69.1; 435/7.1; 514/1
(58) Field of Search ............................ 435/5, 6, 4, 69.1, 435/91.1, 91.2, 7.1; 514/1

(56) References Cited

PUBLICATIONS

Alfonso et al., "A polymorphic variation in a putative regulation box of the TNFA promoter region", *Immunogenetics* 1994 39:150–154.
Coligan et al., "Immunofluroescence and cell Sorting", *Current Protocols in Immunology* 1(2):Chapter 5 1991.
Cooney et al., "Site–Specific Oligonucleotide Binding Represses Transcription of the Human c–myc Gene in Vitro", *Science* 1988 241:456–459.
Dervan et al., "Second Structural Motif for Recognition of DNA by Oligonucleotide–Directed Triple–Helix Formation", *Science* 1991 251:1360–1363.
Chatper 20, Gene Therapy and other Molecular Genetic–based Therapeutic Approaches, in *Human Molecular Genetics*, T. Strachan and A. P. Read, BIOS Scientific Publishers Ltd. 1996.
Fine et al., "A Prediction Rule to Identify Low–Risk Patients with Community–Acquired Pneumonia", *New Engl. J. Med.* 1997 336:243–250.
Hirani and MacFarlane, "Impact of management guidelines on the outcome of severe community acquired pneumonea", *Thorax* 1997 52:17–21.
*British Thoracic Society, Q. J. Med.* 1987.
Lee et al., "Complexes formed by (pyrimidine)η (purine)η DNAs on lowering the pH are three–stranded" *Nucleic Acids Res.* 1979 6:3073–3091.
Leeper and Torres, "Community–Acquired Pneumonia in the Intensive Care Unit", *Clin. Chest. Me.* 1995 16:155–171.
Niederman et al., "Guidelines for the Initial management of Adults with Community–acquired Pneumonia:Diagnosis, Assessment of Severity, and Initial Antimicrobial Therapy", *Am. Rec. Resp. Dis.* 1998 148:1418–1426.
O'Connor, et al. *J. Neurochem.* Oligodeoxynucleotides as Antisense Inhibitors of Gene Expression, CRC Press, Boca Raton, Fla. 1988.
Pachon J. et al., "Severe Community–acquired Pneumonia", *Am. Rev. Resp. Dis.* 1990 142:369–373.
Ruiz M. et al., "Severe Community–acquired Pneumonia", *Am. J. Respir. Crit. Care. Med.* 1999 160:923–929.

*Primary Examiner*—W. Gary Jones
*Assistant Examiner*—Janell E. Taylor
(74) *Attorney, Agent, or Firm*—Licata & Tyrrell P.C.

(57) ABSTRACT

This invention relates to diagnostic methods based upon a particular genotype in the Tumor Necrosis Factor (TNFα) gene, more specifically, GA or AA at the −238 site rather than the GG at this locus. More specifically, this invention relates to a method for diagnosis of increased risk of death in patients with community-acquired pneumonia (CAP) and diagnosing pre-disposition or susceptibility to increased risk of death in patients who develop CAP, by screening for the presence of this polymorphism. The invention also relates to compositions for screening for the polymorphism and improved treatment choices for patients having the polymorphism of the present invention. The invention also relates to screening assays and therapeutic and prophylactic methods.

2 Claims, No Drawings

METHOD OF DIAGNOSING AND TREATING INCREASED RISK OF DEATH FROM COMMUNITY-ACQUIRED PNEUMONIA ASSOCIATED WITH THE A ALLELE OF THE TNFα-238 POLYMORPHISM

This application claims the benefit of priority from provisional U.S. application Ser. No. 60/238,976 filed Oct. 10, 2000.

FIELD OF THE INVENTION

This invention relates to diagnostic methods based upon a particular genotype in the Tumor Necrosis Factor (TNFα) gene, more specifically, a guanine (G) to adenine (A) transition at the −238 site in one of the TNFα genes giving a GA (or adenine adenine genotype, AA) genotype rather than the GG genotype at this locus. More specifically, this invention relates to a method for diagnosis of increased risk of death in patients with community-acquired pneumonia (CAP) and diagnosing pre-disposition or susceptibility to increased risk of death in patients who develop CAP, by screening for the presence of this A allele risk polymorphism. The invention also relates to compositions for screening for the polymorphism and improved treatment choices for patients having the polymorphism of the present invention. The invention also relates to screening assays and therapeutic and prophylactic methods.

BACKGROUND OF THE INVENTION

Pneumonia is a common clinical entity, particularly among the elderly. A thorough understanding of the epidemiology and microbiology of community-acquired pneumonia (CAP) is essential for appropriate diagnosis and management. Although the microbiology of CAP has remained relatively stable over the last decade, there is new information on the incidence of atypical pathogens, particularly in patients not admitted to hospital, and new information on the incidence of pathogens in cases of severe CAP and in CAP in the elderly. Recent studies have provided new data on risk factors for mortality in CAP, which can assist the clinician in decisions about the need for hospital admission. The emergence of antimicrobial resistance in *Streptococcus pneumonia*, the organism responsible for most cases of CAP, has greatly affected the approach to therapy, especially in those patients who are treated empirically. Guidelines for the therapy of CAP have been published by the *American Thoracic Society*, the *British Thoracic Society*, and, most recently, the *Infectious Diseases Society of America* and others. These guidelines differ in their emphasis on empirical versus pathogenic-specific management.

CAP remains a significant health problem and patients continue to die despite receiving appropriate antibiotic therapy. Modification of the host immune response, both anti- and pro-inflammatory approaches, has yet to live up to the promise of improved outcome. Despite this, there is significant reason for optimism. Some immunomodulatory therapies clearly have efficacy in some patients. As the understanding of the immune response to pneumonia improves the ability to tailor specific therapies for individual patients will also improve, hopefully avoiding the deleterious effects that have so far prevented the development of an effective immune based therapy. The possibility of delivering cytokines directly to the lung, is a particularly promising way of achieving the desired pulmonary effect without systemic side effects. Corticosteroids are currently unique in that they have a proven role in the therapy of pneumonia due to *P. carinii*. The development of pathogen specific therapies, such as INF for *L. pneumophila*, based on an improved understanding of host-pathogen interactions, are awaited.

The past 20 years has seen an explosion in our knowledge of human immunology and we are only now beginning to explore the therapeutic possibilities this has made available. The next 10 years promises to finally provide a significant advance in the therapy of pneumonia, the first substantial gain since penicillin.

In light of the prevalence of CAP and the evolution of resistance in the most common bacterial CAP pathogen, physicians advise obtaining specimens for culture of CAP pathogens and analyzing patterns of susceptibility, especially of *S. pneumonia*, in their communities, using antibiotics appropriately and prudently, according to prevailing susceptibilities when empirical treatment is called for, and immunizing susceptible patients with pneumococcal and influenza vaccines. This is because the mortality of patients with severe CAP approaches or may exceed 20%, compared to less than 1% for patients with non-severe CAP (Fine et al. *New Engl. J. Med.* 1997.336:243–238, British Thoracic Society, *Q. J. Med.* 1987.239:192–220, Niederman et al. *Am. Rev. Resp. Dis.* 1993.148:1418–1426). In such cases an ability to improve accuracy of diagnosis of, or predisposition or susceptibility to, severe CAP would be of distinct advantage and may lead to improved outcomes and lower medical costs for such patients.

TNFα acts on many healthy cells in addition to cancer cells and has been widely described in the literature. See e.g., Alfonso et al. *Immunogenetics* 1994.39:150–154. It is important in regulating immune and inflammatory responses and plays a large role in septic shock. It is released by a variety of cells including red and white blood cells, cells that line blood vessels, nervous system cells, muscle cells, bone cells, and some tumor cells. Although it was first observed to kill certain tumor cells (sarcoma cells), TNF has been found to help some tumors grow. In addition, TNF can be very toxic to normal cells. Early experiments found that administering TNF caused fever and loss of appetite. TNF also has been shown to affect the metabolism of many cell types, causing them to need more oxygen. It has been found to play a role in many autoimmune diseases, such as rheumatoid arthritis and myasthenia gravis. Certain viral and bacterial infections can cause healthy cells to produce elevated levels of TNF.

Tumor necrosis factor alpha (TNFα) is a critical component of the host immune response to infection. However TNFα also plays a major role in the clinical manifestations of septic shock, a frequently fatal complication of CAP. A number of polymorphisms in or near the TNFα gene on chromosome 6 have been described. The TNFα −238 polymorphism is a guanine (G) to adenine (A) transition, with the A allele associated with greater TNFα production in-vitro, although this has not been a uniform finding. Carriage of the TNFα-238 A allele has been associated with an increased risk of severe malarial anemia, chronic hepatitis B and C infection, alcoholic steatohepatitis, and psoriasis.

Carriage of the A allele of the TNFα-238 polymorphism is believed to be associated with a greater risk of mortality, and greater risk of septic shock, in patients with CAP. It is a surprising feature of the present invention to be able to identify patients having an increased risk of death from CAP by the method of the present invention thereby identifying more effective treatment options such as pneumococcal and influenza vaccination of such at risk patients.

BRIEF SUMMARY OF THE INVENTION

It is a particular object of the invention to provide a method of identifying predisposition or susceptibility to increased risk of death in patients with CAP. Thus, the invention also relates to compositions for screening for the TNFα A allele, i.e., GA or AA genotype at the −238 site, and improved treatment choices for patients identified at being at risk for an increased risk of death when they have CAP. Subjects with a TNFα AA genotype at the −238 site are believed to be at a similar or greater risk of death than patients with the GA genotype. The invention also relates to screening assays using the TNFα A allele described herein and therapeutic and prophylactic methods discovered using such screening assays.

Other preferred embodiments of the present invention will be apparent to one of ordinary skill in light of the following description of the invention and of the claims.

DETAILED DESCRIPTION OF THE INVENTION

In a first aspect, the invention provides a method of diagnosing a disease condition associated with the A allele (GA or AA genotype) at the −238 site of TNFα. The first aspect of the invention further provides a method of identifying an animal, including a human, predisposed or susceptible to a risk associated with a particular genotype in a TNFα gene, said method comprising determining the genotype of said TNFα gene in said animal. In an embodiment of the invention, the method is to screen for an individual at risk of a condition or disease such as increased risk of death for patients having CAP by identifying the A allele (GA or AA genotype) in TNFα at −238.

A correlation has now been found between the A allele (GA or AA genotype) in the TNFα gene, specifically at position −238, and an increased risk of death in patients with CAP. The invention is of advantage in that by screening for the presence of the polymorphism it is possible to identify individuals likely to have a genetic predisposition or susceptibility to such increased risk. It may also result in substantially different management, especially prevention and treatment (vaccination), if CAP occurs, with subsequent substantial improvement in mortality and morbidity from CAP, especially in at risk populations.

In an embodiment of the invention, diagnosis is carried out by determining whether a TNFα gene contains the GA or AA genotype at −238. Genotypic and allelic frequencies of this invention are readily determined by a number of methods known to those skilled in the art. Examples used in the present invention are provided in Example 1 below and include using PCR amplification and restriction enzyme digestion.

The method conveniently comprises amplifying a fragment of a TNFα gene to produce copies and determining whether copies of the fragment contain the particular genotype GA or AA.

Another suitable technique is to amplify the fragment using PCR techniques, producing copies of a fragment that is at least 500 base pairs in length, preferably at least 600 base pairs in length. It is preferred that the PCR primers are selected so as to amplify a region of the gene that is about 740 base pairs in length. PCR techniques are well known in the art and it would be within the ambit of a person of ordinary skill in this art to identify primers for amplifying a suitable section of the applicable exon of the TNFα gene. PCR techniques are described for example in EP-A-0200362 and EP-A-0201 184. In a further embodiment of the invention, the diagnostic method comprises analysis of the TNFα gene using single strand conformational polymorphism (SSCP) mapping to determine whether the TNFα gene is the risk or the non-risk form, i.e., the A allele at the −238 site.

As described above, in preferred embodiments of the first aspect of the invention, the method comprises screening a TNFα gene, and this screening is conveniently carried out by any one of a number of suitable techniques that are known in the art, and may be conveniently selected from amplification of a nucleic acid sequence located within the TNFα gene, Southern blotting of regions of the gene and single strand conformational polymorphism mapping of regions within the gene or as described in Example 1 below. The genotype in that region is also optionally determined using a variety of methods including hybridization probes adapted selectively to hybridize with the particular polymorphism of the TNFα gene at the −238 location which is associated with predisposition or susceptibility to disease. A probe used for hybridization detection methods must be in some way labeled so as to enable detection of successful hybridization events. This is optionally achieved by in vitro methods such as nick-translation, replacing nucleotides in the probe by radioactively labeled nucleotides, or by random primer extension, in which non-labeled molecules act as a template for the synthesis of labeled copies. Other standard methods of labeling probes so as to detect hybridization are known to those skilled in this art.

According to a second aspect of the invention there is provided a method of diagnosis and therapy comprising diagnosing patients at increased risk of death with CAP according to the method of the first aspect of the invention and treating an individual having such increased risk by methods known to those of skill in the art such as pneumococcal and influenza vaccination and by using the novel treatment and prophylactic methods described below. It is preferable to do so prior to the patient having CAP. CAP can be diagnosed by methods known to those of skill in the art and as described herein.

Known therapies for CAP can be effective in halting advancement of the disease, or at least slowing the advancement. TNFα −238 gene analysis of this invention may also lead to more appropriate preventative measures, such as vaccination, and placement of patients into intensive care/critical care units, an important factor in optimizing survival from CAP. It is thus an advantage of the invention that early identification of patients at increased risk of death with CAP is improved, so that preventative therapy can be started as soon as possible, optimizing any interventions potential (such as vaccination and immunomodulatory therapy) for affecting outcome. The decision of a physician on how and whether to initiate therapy in anticipation of the disease can be taken with increased confidence.

A variety of suitable treatments of patients at increased risk of death from CAP are described in the art and herein. See e.g., Hirani and MacFarlane *Thorax* 1997.52:17–21, Pachon J. et al. *Am. Rev. Resp. Dis.* 1990.142:369–373, Ruiz M. et al. *Am. J. Respir. Crit. Care. Med.* 1999.160:923–929, Leeper and Torres *Clin. Chest. Med.* 1995.16:155–171. Other treatments will be known to persons of skill in the art.

Another aspect of the invention provides a composition for use in diagnosing a disease associated with a genetic polymorphism in a TNFα gene in an individual predisposed or susceptible to said increased risk of death, said composition comprising one or more primer nucleic acid molecules adapted to amplify a portion of a TNFα gene selected from a portion of the gene around the −238 location.

The composition of this aspect of the invention may comprise a nucleic acid molecule capable of identifying the GA −238 genotype (or AA) in said TNFα gene, said genotype being indicative of a risk genotype in said individual.

A further embodiment of the invention provides a composition for identifying individuals at increased risk of death from CAP, comprising means for determining the genotype GA or AA (i.e. the A allele) of a TNFα gene of an individual at the −238 location such as the method provided in Example 1 herein.

In an embodiment of the invention, a composition comprises PCR primers adapted to amplify a DNA sequence within and around the TNFα −238 location, wherein alternative versions of the gene are distinguished one from another, i.e., whether or not the A allele is present.

In a further aspect of the invention there is provided a kit comprising a diagnostic composition such as described above and an indicator composition for indicating how possessing the GA or AA genotype of a TNFα −238 gene correlates with the increased risk of death in patients with CAP.

Diagnostic kits are typically accompanied by or comprise a chart or other visual aid for assistance in interpreting the results obtained using the kit. Suitable indicator compositions for use in the diagnostic kit of the invention include a leaflet or other visual reminder that possessing the risk polymorphism version of a TNFα gene (i.e., GA or AA genotype) correlates with increased risk of death in patients with CAP.

In a still further aspect of the invention there is provided use, in the manufacture of means for diagnosing whether an individual has an increased risk of death from CAP, of PCR primers adapted to amplify a region around −238 in the TNFα gene. Alternative versions of the gene are typically distinguished one from another by means known to those skilled in the art.

Multiple techniques exist and are known to one skilled in the art in the manufacture of means for diagnosing whether an individual has an increased risk of death from CAP by determining the GA or AA genotype or A allele of the gene TNFα at −238, for example, PCR primers adapted to amplify a region around −238 in the TNFα gene. One can use restriction analysis which generates different fragment lengths for the A allele (GA and GG genotype), identified by electrophoresis on an agarose gel where the different fragments migrate differently based on their size.

According to the invention, an individual who is heterozygous (GA) is classified as having an increased risk of death from CAP. Individuals with a AA genotype are believed to be at even higher risk.

Optionally, the assessment of an individual's risk factor according to any aspect of the invention is calculated by determining the genotype of a TNFα gene and combining the result with analysis of other known genetic or physiological or other risk factors known to those of skill in the art. The invention in this way provides further information on which measurement of an individual's risk can be based.

In another embodiment of the invention, the results of the genotyping done herein are used, along with other diagnostic measures and disease parameters, by treatment providers to determine the best course of treatment for the patient having been determined as susceptible to increased risk of death from CAP by the methods of this invention.

The TNFα polypeptide described in the present invention (A allele at the −238 site) may be beneficially employed in a screening process for compounds which stimulate (agonists) or inhibit (antagonists, or otherwise called inhibitors) the synthesis or action of the TNFα polypeptide. The TNFα polypeptide may also be employed in a screening process for compounds which mimic the agonist or antagonist properties of the TNFα polypeptide. Thus, the polypeptide encoded by TNFα (A allele at the −238 site) may also be used to assess and identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al. *Current Protocols in Immunology* 1(2): Chapter 5 (1991).

TNFα proteins are ubiquitous in the mammalian host, including humans, and are responsible for many biological functions, including many pathologies. Accordingly, it is desirous to find compounds and drugs which stimulate TNFα polypeptide (A allele at −238) on the one hand and which can inhibit the function of TNFα polypeptide (A allele at −238) on the other hand.

In general, such screening procedures may involve identifying, generating and using appropriate cells which express the receptor of the TNFα polypeptide on the surface thereof. Such cells include cells from mammals, yeast, Drosophila or *E. coli*. Such cells may be identified, for example, by direct binding methods using radiolabeled or fluorescently tagged TNFα polypeptide (A allele at −238). Cells expressing the TNFα polypeptide receptor (or cell membrane containing the expressed polypeptide) are then contacted with a test compound to observe binding, or stimulation or inhibition of a functional response. Alternatively, the cDNA for the TNFα polypeptide receptor may be cloned by the above direct binding methods using expression cloning or purification methods known in the art, and its extracellular domain expressed as a secreted or membrane protein. The soluble or membrane bound receptor can then be used to identify agonists or antagonists via direct binding methods.

The assays may simply test binding of a candidate compound wherein adherence to the cells bearing the TNFα polypeptide receptor is detected by means of a label directly or indirectly associated with the candidate compound or in an assay involving competition with a labeled TNFα polypeptide. Further, these assays may test whether the candidate compound results in a signal similar to that generated by binding of the TNFα polypeptide, using detection systems appropriate to the cells bearing the TNFα polypeptide receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential TNFα polypeptide antagonists include antibodies or, in some cases, oligonucleotides or proteins which are closely related to the ligands, substrates, receptors, etc., as the case may be, of the TNFα polypeptide, e.g., a fragment of the ligands, substrates, receptors, or small molecules which bind to the target receptor of the present invention but do not elicit a response, so that the activity of the polypeptide is prevented. Preferred are those that can access and effect cellular function.

This invention provides methods of treating an abnormal conditions related to both an excess of and insufficient amounts of TNFα polypeptide (A allele) activity.

If the activity of TNFα polypeptide is in excess as is believed to be the case in the present invention, several approaches are available. One approach comprises administering to a subject an inhibitor compound (antagonist) as herein above described along with a pharmaceutically acceptable carrier in an amount effective to inhibit activation by blocking binding of the TNFα polypeptide to its target receptor, or by inhibiting a second signal, and thereby alleviating the abnormal condition, i.e., increased risk of death with CAP.

In another embodiment, soluble forms of TNFα polypeptides (A allele at −238) capable of binding its receptor in competition with endogenous TNFα polypeptide may be administered. Typical embodiments of such competitors comprise fragments of the TNFα polypeptide.

In still another embodiment, expression of the gene encoding endogenous TNFα polypeptide can be inhibited using expression blocking techniques. Known such techniques involve the use of antisense sequences, either internally generated or separately administered. See, for example, O'Connor, *J. Neurochem.* 1991.56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al. *Nucleic Acids Res.* 1979.6:3073; Cooney et al. *Science* 1988.241:456; Dervan et al. *Science* 1991.251:1360. These oligomers can be administered per se or the relevant oligomers can be expressed in vivo.

For treating abnormal conditions related to an underexpression of TNFα and its activity, several approaches are also available. One approach comprises administering to a subject a therapeutically effective amount of the TNFα polypeptide or a compound, i.e., an agonist or mimetic as described above, in combination with a pharmaceutically acceptable carrier, to thereby alleviate the abnormal condition. Alternatively, gene therapy may be employed to effect the endogenous production of TNFα by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in *Human Molecular Genetics,* T. Strachan and A. P. Read, *BIOS Scientific Publishers* Ltd. (1996).

All such agonists and antagonists are administered in an amounts effective to treat the condition and in pharmaceutically acceptable carriers. Techniques for determining effective amounts and carriers are well known to those of skill in the art.

In a prospective cohort study of patients with CAP described in Example 2, a significant association between TNFα-238 genotype and mortality was found. Carriage of an A allele at the TNFα-238 locus confers a 3.2 times greater risk of fatal outcome than the usual GG genotype. This finding has significant implications for not only the prevention and treatment of CAP, but also for understanding the genetic basis of adverse outcome from infectious diseases.

The non-genetic risk factors for CAP have been extensively studied and subject to meta-analysis. To put the finding of an age adjusted odds ratio of 3.2 in perspective, the meta-analysis found the pooled odds ratio for death from CAP in patients with underlying malignancy to be 2.8, congestive heart failure 2.4, alcohol abuse 1.6, and diabetes only 1.3.

All deaths in patients with TNFα-238 GA genotype were attributed to complications of sepsis, while 37.5% (6/16) of deaths in patients with GG genotype were not directly attributable to the initial infection. The relative risk of infection related mortality may therefore be even higher than the crude mortality rates which were compared.

APACHE II and PSI were used as mortality prognostic indicators in patients with CAP. Significantly higher APACHE II and PSI values were found in subjects with TNFα-238 GA genotype. Serum TNFα levels have been demonstrated to correlate directly with the APACHE II score. Knowledge of the TNFα-238 genotype provided additional prognostic information independent of both the APACHE II and PSI scoring systems.

No subjects with TNFα-238 AA genotype were identified. As the A allele at −238 had a frequency of only 0.05, the expected number of AA homozygotes in the cohort was less than 1 (0.68) if the population was in Hardy-Weingberg equilibrium.

Significantly greater age of subjects with TNFα-238 GA genotype was also observed. Since age is a risk factor for mortality from CAP, this is a potential confounding factor, although multivariate analysis suggests otherwise. It is believed that carriage of the TNFα-238 GA genotype is protective against death from illnesses other than CAP, conferring an overall lifetime survival benefit.

Non-genetic factors such as the length of time to initial therapy and adequacy of therapy are also believed to play important roles in the ultimate outcome of CAP. The length of time from onset of symptoms to presentation was not controlled, but treatment differences between patients with TNFα-238 GG or GA genotype were not evident. As all assessments of outcome were made prior to genotype information being available, and genotyping was performed blinded to the clinical data, the potential for bias towards one genotype was minimized.

Interpreting serum TNFα levels taken at varying time points after the onset of illness and commencement of antibiotics is difficult. Even in patients with acute septic shock, TNFα is not always detectable in the serum. The correlation between serum TNFα levels and tissue concentrations, which are probably biologically more important, is not certain. Knowledge of the presence of a genotype that correlates with an overall phenotypic response is likely to be more useful than the current practice of measuring cytokine levels at a single point during or after CAP has already developed.

Carriage of the GA or AA genotype at TNFα-238 is an independent risk factor for mortality from CAP. In addition, logistic regression analysis suggests that knowledge of TNFα-238 genotype provides prognostic information that is both independent of and additive to the APACHE II and PSI scores. Carriage of the TNFα-238 GA or AA genotype is believed to be an indication for pneumococcal and influenza vaccination regardless of age or underlying disease status. Recognition of the potential role of this polymorphism as an inherited predisposition to death from infection may open new avenues of prevention and treatment for severe infectious diseases.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following Examples, which are included herewith for purposes of illustration only and is not intended to be limiting of the invention.

EXAMPLE 1

Subjects were recruited as part of a prospective cohort study of patients with CAP. Septic shock was defined as a systolic blood pressure of <90 mmHg and at least 4 hours of inotropic support after adequate fluid replacement. Genotype was determined using PCR amplification and restriction enzyme digestion. The significance of trends was assessed using Fishers-exact test.

272 patients were successfully genotyped, 24 patients (8.8%) died, 28 (10.3%) had septic shock. 244 (89.7%) of patients were GG homozygotes, 27 GA (10.3%) heterozygotes and there were no AA homozygotes. Mortality was significantly higher in patients with GA or AA genotype (26% vs 7%, p=0.005, relative risk 3.7). There was no significant difference in the risk of septic shock (14.8% vs 9.8%, p=0.5). In a logistic regression model adjusting for age, sex, underlying cardiac failure, COPD and co-existing malignancy TNFα-238 GA remained an independent risk factor for death (p=0.02) with an adjusted odds ratio of 3.8.

TNFα-238 A allele (GA or AA genotype) carries a significantly greater risk of death from CAP, and is believed to be an indication for pneumococcal and influenza vaccination.

EXAMPLE 2

Subjects in this study were diagnosed with CAP and exhibited symptoms for less than 14 days. The presence of a new chest radiographic infiltrate was confirmed by either a Radiologist or a Pulmonary/Critical Care physician, with clinical features suggestive of acute pneumonia. The clinical features required were one of group A (fever (>37.8° C.), hypothermia (<36.0° C.), cough, sputum production); or two of group B (dyspnea, pleuritic pain, physical findings of lung consolidation, and leukocyte count of >12×10$^9$/L or <4.5× 10$^9$/L).

No patients with severe immunodeficiency as defined by the Center for Disease Control criteria for patients with the Acquired Immune Deficiency syndrome; no patients receiving chemotherapy in the past 60 days; no patients receiving treatment with corticosteroids equivalent to prednisolone >20 mg per day for more than 14 days; no patients receiving immunosuppression following organ transplantation; no patients on cyclosporine, cyclophosphamide or azothioprine; no patients from nursing homes who were non-ambulatory; and no patients hospitalized within the past 30 days were included in the study.

All patients were assessed by a pulmonary physician within 24 hours of presentation. The majority of patients were seen in the Emergency Department at the time of admission. Pneumonia Severity Index (PSI) scores using the clinical data available at the time of presentation were calculated. Acute physiologic and chronic health evaluation (APACHE) II scores were calculated using the worst physiological values during the first 24 hours after presentation. Results of microbiological and other laboratory tests as ordered by the treating physician were recorded. Alcohol consumption was measured using the AUDIT-C questionnaire.

Septic shock was defined using American College of Chest Physicians and Society for Critical Care Medicine criteria. The criteria for septic shock was a documented systolic blood pressure of <90 mmHg for at least 30 minutes in the absence of any other causes of shock, and at least 4 hours of inotropic support after adequate fluid replacement were required. Subjects had to meet these criteria within 48 hours of presentation to hospital to be classified as having septic shock. Patients were classified in a blinded fashion, i.e. without any knowledge of genotype information.

Whole blood for genotypic analysis was collected, transferred into 1.5 ml cryotubes and stored at −70° F. until processed. DNA was extracted from the whole blood samples using the Genomic DNA Purification Kit (Promega, Madison, Wis.). The genotypic analysis was also performed in a blinded fashion, that is, the analysis was performed without knowledge of any clinical data including end points such as mortality, septic shock and respiratory failure.

The region containing the TNFα-238 locus was amplified using the primers TNFα-238-A1 (5'-ATCTGGAGGAAGCGGTAGTG-3'; SEQ ID NO: 1) and TNFα-238-M2 (5'-AGAAGACCCCCCTCGGAACC-3'; SEQ ID NO: 2). The TNFα-238M2 primer contains 2 basepairs (bp) of the MspI recognition sequence at the 3' end including a mismatched cytosine as shown in the C in the TNFα-238-M2 primer sequence. This mismatched cytosine allows for creation of a MspI restriction site (CCGG) when the G allele is present at position −238. A 152 bp fragment in a PCR mixture containing 1 mg of DNA, 0.25 mmol/l each of the primers TNFα-238-A1 and TNFα-238-M2, 1 unit of Taq polymerase, 1×reaction buffer (Promega, Madison, Wis.), 200 mmol/l each of deoxy-adenosine triphosphate, deoxy-cytidine triphosphate, deoxy-guanosine triphosphate, deoxy-thymidine triphosphate was amplified. Reaction conditions were as follows: 35 cycles of denaturation at 94° C. for 60 seconds, annealing at 59° C. for 60 seconds, and extension at 70° C. for 45 seconds followed by 1 cycle at 70° C. for 10 minutes. The amplified DNA was incubated with MspI. The MspI treated fragments were analyzed by electrophoresis in a 4% agarose gel and visualized by ethidium bromide staining. Interpretation was as follows: a single band at 152 bp identified individuals homozygous for an adenine at the TNFα-238 locus; two bands at 133 and 19 bp identified individuals homozygous for a guanine at the TNFα-238 locus; three bands at 152, 133, and 19 bp identified individuals heterozygous at the TNFα-238 locus.

A total of 295 subjects consented to participate in the study. Twenty subjects were subsequently determined to have a diagnosis other than CAP and excluded from analysis. In 17 of the 20 subjects excluded, subsequent review of old chest radiographs revealed that the infiltrate seen on admission was determined to be chronic. The 3 other subjects excluded were also subsequently determined to have a diagnosis other than pneumonia (malignancy—2, pulmonary embolus—1) The mean age of the 275 study patients was 57.9 years (range 18–98). There were 143 (52.0%) female subjects and 132 (48.0%) male subjects, with 152 (55.2%) African American, 122 (44.3%) and one (0.4%) Asian subject. The distribution of subjects by PSI grade was I-37 (13.5%), II-78 (28.4%), III-57 (20.7%), IV-72 (26.2%) and V-31 (11.3%).

A pathogen was identified from blood cultures in 29 patients (10.5%) and from sputum cultures in an additional 12 patients (4.4%), giving an etiological diagnosis in 41 patients (14.9%). The most common pathogens isolated were *Streptococcus pneumoniae, Pseudomonas aeruginos,*

*Streptococcus viridans,* and *Haemophilus influenzae.* Four patients had more than one pathogen identified. An additional 49 patients (17.8%) had negative blood and sputum cultures but the sputum gram stain was consistent with infection due to *S.pneumoniae.* No patient had any pathogen identified resistant to the initial empiric antibiotic regimen they received.

The frequency of the GA genotype in the population was 10.2% (28/275). No subjects were identified with at TNFα-238 AA genotype. The alleles of TNFα-238 within the cohort are in Hardy-Weinberg equilibrium. Table 1 shows a comparison of demographic information, APACHE II scores and PSI scores by genotype at the TNFα-238 locus.

TABLE 1

COMPARISON OF DEMOGRAPHIC INFORMATION AND SEVERITY INDICES BY TNFα-238 GENOTYPE

| Number | TNFα-238 GA 28 | TNFα-238 GG 247 |
|---|---|---|
| Age | 68.4 (13.7) | 56.7 (19.1) |
| Female | 19 (67.9%) | 124 (50.2%) |
| APACHE II score | 15.1 (8.8) | 12.3 (7.9) |
| PSI scare | 98.3 (36.8) | 81.2 (40.6) |
| Mortality | 7 (25%) | 16 (6.5%) |

There were 23 deaths (8.4%), seven in patients with the GA genotype and 16 in the GG group. The relative risk for death in subjects with the GA genotype at TNFα-238 was 3.7 (1.7–8.2). The attributable risk of TNFα-238 GA genotype to mortality within the population studied was 21%. Table 2 shows the causes of death in each TNFα-238 genotype.

TABLE 2

CAUSES OF DEATH BY TNFa-238 GENOTYPE

|  | TNFα-238 GA | TNFα-238 GG |
|---|---|---|
| Septic shock +/− respiratory failure | 4 (57%) | 9 (56%) |
| Respiratory failure without septic shock | 3 (43%) | 1 (6%) |
| Progressive cardiac failure | 0 (0%) | 2 (12%) |
| Sudden event in a clinical improving patient | 0 (0%) | 2 (12%) |
| Other organ failure not related to sepsis | 0 (0%) | 2 (12%) |
| Total deaths | 7 | 16 |

In subjects with no underlying chronic medical conditions the mortality was 25% (1/4) in subjects with TNFα-238 GA genotype, and 2.7% (2/73) in patients with GG genotype (p=0.15). In subjects under the age of 65 the mortality was 11.1% (1/9) with TNFα-238 GA genotype and 3.4% (5/146) with GG genotype (p=0.3). However in subjects over the age of 65 the mortality was significantly higher with carriers of GA genotype, 6/18 (33.3%) vs 11/96 (11.5%), p=0.03.

There was no significant difference in the frequency of bacteremia between genotypes (GA 10.7%, GG 10.5%).

Multivariate analysis incorporating all the chronic health factors that may be contributing to mortality found only TNFα-238 GA genotype (p=0.03), increasing age (p=0.008) and underlying cerebrovascular disease (p=0.03) to be independent predictors of mortality. As age and cerebrovascular disease may be confounding factors, a nominal logistic regression was used to calculate the odds ratio for mortality associated with TNFα GA genotype adjusted for these two factors. The adjusted odds ratio remained highly significant at 3.2 (1.1–8.9).

As would be expected, both the initial PSI score (p<0.0001) and the APACHE II score (p<0.0001) were significant predictors of fatal outcome. To determine whether knowledge of TNFα-238 genotype would provide clinicians with additional prognostic information not accounted for by either the PSI or APACHE II scores, a logistic regression analysis was performed incorporating both of these indices with TNFα-238 genotype. In the APACHE II/TNFα-238 model, TNFα-238 GA genotype remained an independent predictor of mortality (p=0.01) with an APACHE II adjusted odds ratio for death of 5.0 (1.5–16.1). In the PSI/TNFα-238 model, TNFα-238 GA genotype still remained an independent predictor of mortality (p=0.009) with a PSI adjusted odds ratio for death of 4.4 (1.4–13.5).

Twenty eight (10.2%) subjects met the criteria for septic shock. There was no significant difference in the risk of septic shock in subjects with the TNFα-238 GA genotype (14.3% vs 9.7%, p=0.5). In subjects with septic shock, the mortality was 100% (4/4) in carriers of the TNFα-238 GA genotype, compared to 41.7% (10/24) with TNFα-238 GG genotype (p=0.10).

Two hundred and seven (75.3%) subjects had at least 2 blood cultures prior to antibiotics. In these 207 subjects, the risk of bacteremia in patients with TNFα-238 GA genotype was 15.0% compared to 13.9% in subjects with TNFα-238 GG genotype (p=1.0).

Statistical calculations were performed using the statistical package JMP version 3.2.2 (SAS Institute Inc.) Unless otherwise stated, results are expressed as mean +/−standard deviation. Relative risks are reported as RR (95% confidence intervals). The statistical significance of differences in continuous variables were calculated using Student's t-test and for categorical variables with Fisher's exact test. The significance of trends was assessed using Chi-squared analysis. Attributable risk was calculated using published formula. All reported p values are two-tailed with a value of <0.05 considered significant. To investigate the relationship between mortality, TNFα-238 genotype, and other known clinical risk factors for adverse outcome from CAP, logistic regression analysis was used. A stepwise logistic regression analysis incorporating TNFα-238 genotype and age, sex, race, a history of cardiac disease, renal disease, chronic obstructive pulmonary disease, liver disease, cerebrovascular disease, neoplastic disease, and excess alcohol consumption was performed. The calculated odds ratios and 95% confidence intervals after adjusting for confounding factors are expressed as an approximation of relative risk.

What is claimed is:

1. A method of identifying an individual at an increased risk of death from community-acquired pneumonia (CAP) associated with the A allele in a TNFα gene at the −238 locus, said method comprising determining the genotype of said TNFα gene in an individual; and identifying increased risk of death from CAP based on said genotype.

2. A method of treating patients comprising identifying a patient at an increased risk of death from community-acquired pneumonia (CAP) by identifying the A allele in a TNFα gene at the −238 locus in such patient; and vaccinating such patients prior to the onset of CAP with pneumococcal, influenza or a combined pneumococcal/influenza vaccination.

* * * * *

SEQUENCE LISTING

<160> NUMBER OF SEQ ID NOS: 2

<210> SEQ ID NO 1
<211> LENGTH: 20
<212> TYPE: DNA

-continued

```
<213> ORGANISM: Artificial Sequence
<220> FEATURE:
<223> OTHER INFORMATION: Description of Artificial Sequence:  Synthetic

<400> SEQUENCE: 1
atctggagga agcggtagtg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 2
agaagacccc cctcggaacc                                              20
```